United States Patent [19]
Taylor et al.

[11] Patent Number: 5,330,826
[45] Date of Patent: Jul. 19, 1994

[54] PREPARATION OF CERAMIC-METAL COATINGS

[75] Inventors: Timothy E. Taylor; Clyde Riley, both of Huntsville; William R. Lacefield, Jr., Brimingham, Harold D. Coble; George W. Maybee, both of Huntsville, all of Ala.

[73] Assignee: McDonnell Douglas Corporation, Long Beach, Calif.

[21] Appl. No.: 565,936

[22] Filed: Aug. 13, 1990

[51] Int. Cl.$^5$ .............................................. B32B 5/32
[52] U.S. Cl. ..................................... 428/216; 428/336; 428/407; 428/472; 428/704; 428/621; 428/632; 428/655; 428/660; 623/16; 623/12; 623/13
[58] Field of Search ................... 623/16, 23, 22; 428/688, 457, 704, 471, 469, 336, 472, 216, 621, 632, 655, 660

[56] References Cited

U.S. PATENT DOCUMENTS

| | | | |
|---|---|---|---|
| 3,890,107 | 6/1975 | White et al. | 428/613 |
| 3,945,893 | 3/1976 | Ishimori et al. | 204/16 |
| 4,146,936 | 4/1979 | Aoyagi | 623/23 |
| 4,309,488 | 1/1982 | Heide et al. | 623/13 |
| 4,556,389 | 12/1985 | Ueno et al. | 428/469 |
| 4,623,553 | 11/1986 | Ries | 427/2 |
| 4,684,555 | 8/1987 | Neumeyer | 428/469 |
| 4,722,870 | 2/1988 | White | 623/16 |
| 4,770,943 | 9/1988 | Hakamatsuka et al. | 428/471 |
| 4,813,959 | 3/1989 | Cremascoli | 623/23 |
| 4,847,163 | 7/1989 | Shimamune | 428/469 |
| 4,960,646 | 10/1990 | Shimamune et al. | 428/471 |

FOREIGN PATENT DOCUMENTS 2755751  6/1978  Fed. Rep. of Germany ... 623/16 D

*Primary Examiner*—A. A. Turner
*Attorney, Agent, or Firm*—Max Geldin

[57] ABSTRACT

A metal substrate, e.g. titanium, having a calcium phosphate coating, particularly hydroxylapatite, and containing a metal such as cobalt, codeposited on the substrate by electrolyzing a cobalt salt, particularly cobalt sulfate, liquid electrolyte having a calcium phosphate material, particularly hydroxylapatite, suspended therein, employing a cobalt anode and the metal substrate as cathode. The particles of cobalt so codeposited with the particles of calcium phosphate material, e.g. hydroxylapatite, hold the latter particles strongly on the substrate metal. If desired, a second coating of the pure calcium phosphate material, e.g. "hydroxylapatite", optionally can be applied over the codeposited hydroxylapatite-cobalt coating. The calcium phosphate coated metal substrate of the invention, particularly the codeposited "hydroxylapatite"-cobalt coating, on a titanium or cobalt-chromium substrate, has particular value for application as medical implants, e.g. as hip prosthetics, and for high temperature high stressed applications.

17 Claims, No Drawings

PREPARATION OF CERAMIC-METAL COATINGS

BACKGROUND OF THE INVENTION

This invention relates to metal substrates containing a ceramic coating, and is particularly directed to metal substrates such as titanium, containing an electrodeposited coating of a ceramic material, especially hydroxylapatite or similar calcium phosphate material, and cobalt, and having particular applicability as medical surgical implants.

The medical profession has been trying to develop a successful long term human implant for many years, and has yet to develop one that will last for 7 to 10 years in high stressed locations, e.g. hip prostheses and dental implants. The short service time before failure is of special concern in the case of younger patients as additional surgical operations are necessary.

Numerous techniques have been tried but none have been proven successful due to the loss of structural bonding between the human tissues and the metal substrate (implant). Loosening of the implant in the surrounding bone, leads to pain, and requires surgical removal in replacement of the device. Also, adverse tissue reaction is a problem due to the exposed metallic surface, which in time will corrode and release metallic ions which cause damage to the surrounding tissue.

Metal substrates such as titanium alloys have heretofore been coated with hydroxylapatite by various processes such as plasma spraying, ion sputter deposition and electrophoretic deposition in an attempt to obtain chemical bonding to the bone surrounding the implant, thus stabilizing the device.

A primary drawback of all such ceramic coatings has been the lack of strength of the bond between the ceramic, e.g. hydroxylapatite, material and the metal substrate. Further, each of the coatings produced by the above processes has proven unsatisfactory for various reasons such as low bond strength, variation in density, lack of crystallinity, low durability and high cost.

U.S. Pat. No. 3,945,893 to Ishimori et al discloses forming a low-abrasion surface on a metal base member by dispersing fine particles of a hard material in a metal plating solution, immersing in such solution a metal object to be coated as a cathode together with a metal rod as an anode, and passing current through the bath to codeposit a coating of the anode metal and fine particles of the hard material on the metal base member. According to a preferred embodiment, powdered silicon carbide is dispersed in a nickel plating solution such as a nickel sulfamate bath, and an aluminum alloy base member is immersed as a cathode in the bath and a nickel rod as an anode. A current is passed through the bath and a plated coating of nickel and silicon carbide is formed on the aluminum alloy base member. The metal deposit thus formed on the base metal surface is then subjected to polishing to remove a given thickness of the metal coating, leaving the hard fine particles partly exposed and protruded from the deposited layer.

One object of the present invention is to provide both smooth and porous surfaced metal substrates with ceramic coatings, particularly a calcium phosphate coating, so that the resulting ceramic coated substrates have good bond strength and the coating is uniform and durable.

Another object of the invention is the provision of metal substrates such as titanium and its alloys, containing a coating including hydroxylapatite as ceramic material, and a metal, and having characteristics suitable for use as medical implants, including hip prostheses and dental endosseous subperiosteal implants, permitting human tissues to attach and grow onto the coating and insure a strong structural bond between the human tissue and the ceramic coating, free from adverse tissue reaction, and such that the implant will be durable and have an indefinite life.

Still another object is to provide ceramic coated substrates of the above type, wherein the ceramic, particularly hydroxylapatite, is co-deposited with a metal on the substrate, e.g. titanium substrate, to aid in holding the ceramic to the metal.

Yet another object is the provision of a procedure for depositing a coating containing a calcium phosphate ceramic material, e.g. hydroxylapatite, on the substrate.

A still further object is to provide a process for co-depositing the ceramic material, particularly hydroxylapatite, and a metal, particularly cobalt, on the metal substrate.

SUMMARY OF THE INVENTION

According to the invention, the above objects are achieved by providing a substrate such as titanium or an alloy thereof, containing an electrodeposited coating of a calcium phosphate material such as hydroxylapatite and a metal such as cobalt, resulting in a ceramic coated metal substrate having a strong interfacial bond between the substrate and the coating and having particularly advantageous characteristics for application as medical implants.

The above ceramic coated substrate is provided by a process which includes forming a solution of a metal salt such as a cobalt salt, e.g. cobalt sulfate, containing particles of a calcium phosphate material such as hydroxylapatite. The solution containing suspended particles of such calcium phosphate material is electrolyzed, that is subjected to electrolysis, using a metal anode such as a cobalt anode and a cathode formed of a metal substrate material such as titanium or an alloy thereof. A coating is electrodeposited on the metal substrate in the form of a co-deposit of the calcium phosphate material, e.g. hydroxylapatite, and a metal such as cobalt. The co-deposited metal, e.g. cobalt, functions to secure the calcium photphate material to the substrate and to increase the bond strength therebetween.

If desired, a second coating of the pure calcium phosphate material, e.g. hydroxylapatite, can be deposited over the interfacial electrodeposited co-deposit of calcium phosphate material and metal such as cobalt, to create an even thicker calcium phosphate or hydroxylapatite layer for increased biocompatibility. Such second coating can be applied by various processes such as by plasma spray deposition. The resulting coated substrate can then be sintered, if desired.

In addition to medical implants, the invention concept has numerous applications for metals requiring ceramic surfaces, such as for high temperature/high stressed applications. More specifically, additional applications include the fields of friction reduction, conductivity reduction for thermal and electrical applications, metal surface protection from high temperature oxidation, and formation of thin ductile surface undercoatings.

DETAILED DESCRIPTION OF THE INVENTION AND PREFERRED EMBODIMENTS

In the electrolysis process of the invention, the metal substrate to which the codeposit of calcium phosphate material and metal such as cobalt is to be applied and which functions as the cathode in the electrolysis cell, can be titanium or an alloy thereof, such as Ti-6Al-4V, stainless steel, e.g. 316 stainless steel, or a cobalt-chromium alloy such as the cobalt-chromium alloy also including molybdenum, and marketed as Vitallium and Zimaloy. Both commercially pure (CP) titanium, or alloys thereof, and cobalt-chromium are approved FDA metals and alloys for medical implants. The cobalt-chromium substrate provides an even stronger bond with the calcium phosphate material where cobalt is employed as a codeposit with the calcium phosphate material according to the invention.

In the electrolytic process of the invention, the anode can be a metal such as cobalt, nickel, chromium or rhodium, the preferred anode material being cobalt.

The ceramic material which is electrolytically deposited with the metal, e.g. cobalt, on the metal substrate to form the codeposited interface bonding layer, is a calcium phosphate material. A preferred form of the calcium phosphate material is apatite, a natural calcium phosphate usually containing fluorine, sometimes with chlorine, hydroxyl or carbonate substituting for part or all of the fluorine. A particularly preferred apatite is hydroxylapatite, having the formula $Ca_{10}(PO_4)_6(OH)_2$. Another suitable calcium phosphate is tricalcium phosphate, $Ca_3(PO_4)_2$. The terms "ceramic" material and "calcium phosphate" material as employed herein are intended to denote any of the foregoing materials.

The calcium phosphate material in particulate form, e.g. hydroxylapatite, is mixed in suspension in the electrolyte, e.g. cobalt sulfate, and in which the anode, e.g. cobalt, and the metal substrate, e.g. titanium, are suspended, the metal substrate functioning as cathode and spaced appropriately from the anode. The size of the calcium phosphate material particles can range from about 0.1 to about 100 microns, and such particles are maintained in suspension in the electrolyte by suitable stirring. The electrolyte is a solution of a salt of the anode metal, e.g. a cobalt salt such as cobalt sulfate, and contains the suspended calcium phosphate particles. Other cobalt salts, e.g. cobalt sulfamate or cobalt tetrafluoborate can be used where the anode is cobalt. Where the anode metal is nickel, chromium or rhodium, the liquid electrolyte can be, for example, a solution of nickel sulfate, nickel sulfamate, chromium sulfate or rhodium sulfate.

Aqueous solutions of the anode metal salts, e.g. an aqueous solution of cobalt sulfate, can be used as electrolyte. However, solutions of the anode metal salt in organic media also can be employed as electrolyte, such as a solution of cobalt sulfate in methanol. The concentration of the anode metal salt in the electrolyte bath can vary, and generally ranges from about 200 to about 500 grams per liter.

The concentration of suspended ceramic material, e.g. hydroxylapatite, in the electrolyte bath can range from about 5 to about 300 grams of ceramic material, per liter of electrolyte.

The electrolysis is carried out at a voltage sufficient to obtain a current density ranging from about 5 to about 100 mA/cm$^2$, depending on the deposition conditions, e.g. a voltage ranging from about 0.5 to about 20 volts. The temperature of the electrolyte bath can be maintained within a temperature range of about 20° to about 50° C., and duration of the electrolysis operation is from about 30 to about 90 minutes, e.g. about 60 minutes. The electrolyte, e.g. cobalt sulfate bath, is maintained under acidic conditions at a pH of about 1 to about 5. For example for the codeposition of cobalt and hydroxylapatite, the pH of the cobalt sulfate electrolyte is maintained at about 3.8. Low speed stirring of the electrolyte suspension is maintained during electrolysis to prevent agglomeration and sedimentation of ceramic particles in the liquid electrolyte.

As a typical example utilizing a cobalt anode and cobalt sulfate electrolyte, during electrolysis, cobalt particles are released from the cobalt anode, as positive ions, and such particles travel through the cobalt sulfate electrolyte, toward the metal substrate cathode, e.g. titanium or titanium alloy. The calcium phosphate material, e.g. hydroxylapatite, suspended in the electrolyte, and near the cathode surface codeposits with the cobalt on the surface of the metal substrate cathode. The particles of cobalt so codeposited with the particles of ceramic material, e.g. hydroxylapatite, hold the latter particles strongly on the substrate metal. The mixture of the calcium phosphate material, e.g. hydroxylapatite, and metal such as cobalt, electrolytically codeposited on the metal substrate cathode is generally about a 50—50 mixture by weight of the metal, e.g. cobalt, and the calcium phosphate particles, but this can vary, depending upon conditions of electrolysis and the concentration of the suspended calcium phosphate particles in the cobalt salt electrolyte. The thickness of the resulting codeposited calcium phosphate, e.g. hydroxylapatite, and metal such as cobalt coating can vary, for example, from about 5 to about 50 microns. The coating is highly adherent, dense and uniform.

Although the electrodeposited codeposited, e.g. hydroxylapatite-metal coating on the metal, e.g. titanium, substrate is effective per se and has the physical characteristics rendering the resulting substrate containing the ceramic, particularly hydroxylapatite,-cobalt, deposit suitable for application as improved medical implants, particularly in hip prosthetics, an outer coating of the substantially pure calcium phosphate material, e.g. hydroxylapatite, can be applied optionally over the codeposited hydroxylapatite-cobalt coating, to provide a pure layer of hydroxylapatite on the surface, if desired. Such outer coating can be applied, for example, by plasma spraying, ion sputter deposition, or electrophoresis deposition.

Employing plasma spraying, the ceramic, i.e., calcium phosphate, e.g. hydroxylapatite powder, is propelled through a high temperature arc discharge equal to or greater than 10,000° C., forming an additional hydroxylapatite coating on the initially electrodeposited calcium phosphate-cobalt coating on impact. When employing ion sputter deposition, an ion beam is used to sputter off atoms from the calcium phosphate material, e.g. hydroxylapatite, "target" in vacuum, and the sputtered material slowly forms a coating on the initially electrodeposited hydroxylapatite-cobalt, codeposited coating on the substrate. The resulting pure, e.g. hydroxylapatite, overcoating is a dense porous coating. When employing electrophoretic deposition, the hydroxylapatite particles are charged to a potential of about 90 volts in isopropyl alcohol. The particles then drift toward the substrate and attach to the surface.

The thickness of the overall coating of electrodeposited codeposit, e.g. of hydroxylapatite-cobalt, and the top coating of pure hydroxylapatite can range from about 20 to about 2000 microns. Where hydroxylapatite is employed as the calcium phosphate material, the total thickness preferably is not more than 100 microns, and can range from about 20 to about 100 microns. The above plasma spraying, ion sputter and electrophoretic deposition techniques, as well as chemical vapor deposition, are known in the art, and hence further details thereof are not included herein.

As a further optional step, if desired, the substrate containing the codeposited, e.g. hydroxylapatite-cobalt, first layer and the second layer coating of pure hydroxylapatite can be sintered by heating to harden the overall coating. Thus, for example a metal, e.g. titanium, substrate containing an electrodeposited hydroxylapatite-cobalt initial layer and a pure hydroxylapatite second layer coating can be sintered at 600° C. or higher in a vacuum.

The following examples 1 to 7 are examples of practice of the invention. The data and parameters listed below in each of examples 1 to 7 applies to an electrolytic apparatus or cell in the form of a cylindrical container containing a metal salt electrolyte, e.g. a cobalt sulfate, bath in the form of an aqueous solution containing 285 grams per liter of the metal salt, and having particles of hydroxylapatite suspended in the bath, in a concentration of about 10 grams of hydroxylapatite per liter of electrolyte, e.g. cobalt sulfate. The hydroxylapatite material is maintained in suspension in the electrolyte bath by a stirrer mounted in the bottom of the container. A metal, e.g. cobalt, tube serving as anode is mounted centrally in the container, immersed completely in the metal salt suspension of the hydroxylapatite particles. A metal substrate serving as cathode is mounted axially within the tubular metal, e.g. cobalt, anode and suspended in the electrolyte-hydroxylapatite particles suspension, the cathode being spaced from the anode. The metal anode and the metal substrate cathode are connected to a suitable power source.

In each of the examples 1 to 7 below, following electrolysis, a strong durable coating of an electrodeposited codeposit of hydroxylapatite and metal, e.g. cobalt or other anode metal, is formed on the metal substrate cathode, having a thickness between 5 and 50 microns.

EXAMPLE 1

| | |
|---|---|
| Substrate Material (cathode): | Titanium |
| Coating Material: | Hydroxylapatite |
| Current Density: | 10 mA/cm$^2$ |
| Voltage: | 0.9 volts |
| Cobalt sulfate bath: | pH 3.8 |
| Duration of codeposition: | 60 minutes |
| Temperature: | 20° C. |
| Stirring: | low speed |
| Anode: | Cobalt |
| Distance between cathode/anode: | 2 cm |

EXAMPLE 2

| | |
|---|---|
| Substrate Material (cathode): | Cobalt-Chromium-molybdenum |
| Coating Material: | Hydroxylapatite |
| Current Density: | 10 mA/cm$^2$ |
| Voltage: | 0.9 volts |
| Cobalt sulfate bath: | pH 3.8 |
| Duration of codeposition: | 55 minutes |
| Temperature: | 24° C. |
| Stirring: | low speed |
| Anode: | Cobalt |
| Distance between cathode/anode: | 2 cm |

EXAMPLE 3

| | |
|---|---|
| Substrate Material (cathode): | 316 Stainless Steel |
| Coating Material: | Hydroxylapatite |
| Current Density: | 10 mA/cm$^2$ |
| Voltage: | 0.85 volts |
| Cobalt sulfate bath: | pH 3.7 |
| Duration of codeposition: | 45 minutes |
| Temperature: | 24° C. |
| Stirring: | low speed |
| Anode: | Cobalt |
| Distance between cathode/anode: | 2 cm |

EXAMPLE 4

| | |
|---|---|
| Substrate Material (cathode): | Titanium |
| Coating Material: | Hydroxylapatite |
| Current Density: | 10 mA/cm$^2$ |
| Voltage: | 0.9 volts |
| Cobalt sulfamate bath: | pH 3.8 |
| Duration of codeposition: | 60 min |
| Temperature: | 22° C. |
| Stirring: | low speed |
| Anode: | Cobalt |
| Distance between cathode/anode: | 2 cm |

EXAMPLE 5

| | |
|---|---|
| Substrate Material (cathode): | Titanium |
| Coating Material: | Hydroxylapatite |
| Current Density: | 10 mA/cm$^2$ |
| Voltage: | 1.5 volts |
| Nickel sulfate bath: | pH 3.8 |
| Duration of codeposition: | 50 minutes |
| Temperature: | 21° C. |
| Stirring: | low speed |
| Anode: | Nickel |
| Distance between cathode/anode: | 1.2 cm |

EXAMPLE 6

| | |
|---|---|
| Substrate Material (cathode): | 316 Stainless Steel |
| Coating Material: | Hydroxylapatite |
| Current Density: | 10 mA/cm$^2$ |
| Voltage: | 0.85 volts |
| Rhodium sulfate bath: | pH 3.7 |
| Duration of codeposition: | 45 minutes |
| Temperature: | 24° C. |
| Stirring: | low speed |
| Anode: | Rhodium |
| Distance between cathode/anode: | 2 cm |

EXAMPLE 7

| | |
|---|---|
| Substrate Material (cathode): | Titanium |
| Coating Material: | Hydroxylapatite |
| Current Density: | 10 mA/cm$^2$ |
| Voltage: | 0.9 volts |
| Chromium sulfate bath: | pH 3.8 |
| Duration of codeposition: | 60 minutes |
| Temperature: | 22° C. |
| Stirring: | low speed |
| Anode: | Chromium |
| Distance between cathode/anode: | 2 cm |

The following are further examples of practice of the invention.

EXAMPLE 8

The titanium substrate containing the electrodeposited hydroxylapatite-cobalt coating formed in Example 1 is subjected to plasma spraying using hydroxylapatite powder propelled through a high temperature arc discharge in excess of 10,000° C. to form a dense and pure hydroxylapatite coating over the electrodeposited hydroxylapatite-cobalt coating. The overall thickness of the dual coating on the titanium substrate is between 20 and 100 microns.

EXAMPLE 9

The dual coated titanium substrate of Example 8 is subjected to sintering by heating to 600° C. for 2 hours to provide a hardened coating and a strengthened structural bond between such coating and the titanium substrate.

From the foregoing, it is seen that the invention provides a novel and improved combination of metal substrate, e.g. titanium, and calcium phosphate coating, particularly hydroxylapatite, containing certain metals, e.g. cobalt, codeposited by an electrolytic procedure that consists of electrolyzing a metal salt, particularly a cobalt salt such as cobalt sulfate, the electrolyte bath having calcium phosphate material, particularly hydroxylapatite, suspended therein, employing a metal, e.g. cobalt, anode and the metal substrate as cathode. There is no teaching in above U.S. Pat. No. 3,945,893 of the use of particles of a calcium phosphate, particularly hydroxylapatite, and electrolytically codepositing such phosphate together with a metal, particularly cobalt, on a metal substrate, e.g. titanium or a cobalt-chromium alloy, and obtaining a coated substrate having the particular advantages and properties noted below.

The coated metal substrate of the invention, particularly the codeposited hydroxylapatite-cobalt coating, on a titanium or cobalt-chromium substrate, has particular value for application as medical implants, e.g. as hip prosthetics, dental implants, and artificial heart surfaces to minimize the chance of adverse tissue reactions and in some cases to provide chemical bonding to the surrounding bone. Such coated substrates also have important utility in high temperature/high stressed applications including temperature/high stressed applications including hyper velocity projectiles requiring ablating surfaces, reduced friction and electroconductivity, and including aerospace engine parts. Such coated substrates are also useful for computer hardware where metallic surfaces give off damaging electrical charges.

When employed for medical implants the ceramic calcium phosphate coated substrates of the invention, particularly utilizing hydroxylapatite, provide the strong chemical bonding and in some cases sufficient porosity that will allow the human tissues to attach and grow onto the codeposited metal-calcium phosphate, particularly cobalt-hydroxylapatite, coating. This tissue attachment and/or ingrowth will insure a strong chemical and/or mechanical bond between the human body and such coating so that the implant will have an indefinite life. The metal-calcium phosphate, e.g. cobalt- hydroxylapatite, coating will also help to solve the problem of adverse tissue reaction due to the continuous layer of such coating over the metal substrate.

The formation of codeposits on metal substrates according to the invention has surface preparation applications in numerous other areas. These include dry lubrication for surfaces subject to frictional loads such as dry bearings, prevention of high temperature oxidation in hostile environments using surface protective coatings, and providing reduced image distortion in reflective surfaces of mirrors using various ceramic coatings.

Since various changes and modifications of the invention will occur to those skilled in the art within the spirit of the invention, the invention is not to be taken as limited except by the scope of the appended claims.

What is claimed is:

1. An article comprising a substrate consisting essentially of a material selected from the group consisting of titanium and alloys thereof, stainless steel and cobalt-chromium alloy, containing a coating of a calcium phosphate and a metal selected from the group consisting of cobalt, nickel, chromium and rhodium, said coating of calcium phosphate and said metal being in the form of particles of said metal electrolytically codeposited with particles of said calcium phosphate on said substrate, the size of the calcium phosphate particles ranging from about 0.1 to about 100 microns.

2. The article of claim 1, wherein said calcium phosphate is apatite.

3. The article of claim 1, and including a second coating of said calcium phosphate in substantially pure form over said coating of calcium phosphate and said metal.

4. The article of claim 1, wherein said metal is cobalt.

5. The article of claim 4, said coating containing an approximately 50—50 mixture by weight of cobalt and said calcium phosphate.

6. The article of claim 4, wherein said substrate is a cobalt-chromium-molybdenum alloy and said calcium phosphate is hydroxylapatite.

7. The article of claim 6, and including a second coating of substantially pure hydroxylapatite over said coating of hydroxylapatite and cobalt, the total coating thickness ranging from about 20 to about 100 microns.

8. The article of claim 6, in the form of a medical implant.

9. The article of claim 4, and including a second coating of said calcium phosphate in substantially pure form over said coating of cobalt and said calcium phosphate.

10. The article of claim 4, in the form of a medical implant.

11. The article of claim 10, wherein said calcium phosphate material is hydroxylapatite.

12. The article of claim 11, wherein said medical implant is a hip prosthetic.

13. The article of claim 1, the thickness of said coating ranging from about 5 to about 50 microns.

14. An article comprising a substrate consisting essentially of the titanium alloy Ti-6Al-4V containing a coating of hydroxylapatite and cobalt, said coating of hydroxylapatite and cobalt being in the form of particles of cobalt electrolytically codeposited with particles of said hydroxylapatite on said substrate, the size of the hydroxylapatite particles ranging from about 0.1 to about 100 microns.

15. The article of claim 14, and including a second coating of substantially pure hydroxylapatite over said coating of hydroxylapatite and cobalt, the total coating thickness ranging from about 20 to about 100 microns.

16. The article of claim 14, in the form of a medical implant.

17. An article comprising a substrate consisting essentially of a titanium alloy containing a coating of hydroxylapatite and cobalt, said coating of hydroxylapatite and cobalt being in the form of particles of cobalt electrolytically codeposited with particles of said hydroxylapatite on said substrate, the size of the hydroxylapatite particles ranging from about 0.1 to about 100 microns.

* * * * *